United States Patent [19]

Callahan et al.

[11] 4,008,326

[45] Feb. 15, 1977

[54] SUBSTITUTED UREAS AND THIOUREAS AND PHARMACEUTICAL COMPOSITIONS THEREOF

[75] Inventors: William A. Callahan, Richland; Eldridge Myles Glenn, Kalamazoo; Douglas L. Rector, Parchment, all of Mich.

[73] Assignee: The Upjohn Company, Kalamazoo, Mich.

[22] Filed: June 25, 1975

[21] Appl. No.: 590,272

Related U.S. Application Data

[63] Continuation-in-part of Ser. No. 428,372, Dec. 26, 1973, abandoned.

[52] U.S. Cl. .................. 424/263; 260/294.8 C; 260/294.8 H; 260/295 E; 260/295 F; 260/295.5 D; 260/295.5 B
[51] Int. Cl.² ............. A61K 31/395; C07D 213/75
[58] Field of Search ......... 260/294.8 C, 295.5 B, 260/295 F, 294.8 H, 295 E, 295 T, 295.5 T; 424/263

[56] References Cited

OTHER PUBLICATIONS

Novikov et al., Chem. Abstracts, vol. 70, (1) 3776p Jan. 6, 1969.
Chem. Abstracts, Eighth Collective Index, Subjects Triplet–Z, p. 32,479S (1967–1971).

Primary Examiner—Alan L. Rotman
Attorney, Agent, or Firm—Martin B. Barancik; Roman Saliwanchik

[57] ABSTRACT

A method of improving the endogenous production of prostaglandins by a mammal is disclosed, which comprises administering to the mammal an effective amount of 1-pyridylalkyl-3-naphthyl-2(thio)ureas. Disclosed also are novel substituted 1-pyridylalkyl-3-naphthyl-2(thio)ureas and therapeutic compositions thereof which are useful in carrying out the method of the invention.

Disclosed also are methods of treating mammals for clinical conditions responsive to prostaglandins, such as, for example, male infertility, epidermal injuries, atonic uterine bleeding, thromboembolic disease and like clinical conditions.

15 Claims, No Drawings

SUBSTITUTED UREAS AND THIOUREAS AND PHARMACEUTICAL COMPOSITIONS THEREOF

CROSS-REFERENCE TO RELATED APPLICATIONS

This application is a continuation-in-part application of our co-pending application Ser. No. 428,372, filed Dec. 26, 1973 and now abandoned.

BACKGROUND OF THE INVENTION

1. Field of the Invention

The invention is concerned with the production of endogenous prostaglandins by mammals and, more specifically, concerns a method of raising prostaglandin production levels in the mammal by administering 1-pyridylalkyl-3-naphthyl-2(thio)ureas.

The invention also concerns a novel group of substituted 1-pyridylalkyl-3-naphthyl-2-(thio)ureas and therapeutic compositions thereof.

2. Description of the Prior Art

Natural prostaglandins are a well-known group of physiologically active unsaturated hydroxy-substituted fatty acids which are biosynthesized endogenously by mammals such as, for example, canines, bovines, equines, swine, and humans. Identified roles of the natural prostaglandins in mammalian physiology are illustrated by their action as mediators in the inflammatory process, as tonal agents in effecting the contractility of smooth muscle and as activators in a wide variety of mammalian reproductive processes.

Structurally, the natural prostaglandins have been arbitrarily classified into four basic families termed "PGE", "PGF", "PGA" and "PGB", respectively. The various families are composed of differing analogs and stereoisomers having as a hypothetical parent structure, prostanoic acid. For example, the principal members of the PGE family are $11\alpha,15$-dihydroxy-9-ketoprosta-13-enoic acid (referred to alternatively for convenience as "$PGE_1$"); $11\alpha$-15-dihydroxy-9-keto-prosta-4,13-dienoic acid (hereinafter referred to alternatively as "$PGE_2$"); and $11\alpha$-15-dihydroxy-9-keto-prosta-5,13,17-trienoic acid (referred to alternatively for convenience as "$PGE_3$"). The principal members of the PGF family are $9\alpha,11\alpha,15$-trihydroxy-prosta-13-enoic acid (referred to alternatively for convenience as "$PGF_{1\alpha}$"); $9\beta,11\alpha,15$-trihydroxy-prosta-13-enoic acid (referred to alternatively for convenience as "$PGF_{1\beta}$"); $9\alpha,11\alpha,15$-trihydroxy-prosta-5,13-dienoic acid (hereinafter referred to alternatively for convenience as "$PGF_{2\alpha}$"); $9\beta,11\alpha,15$-trihydroxy-prosta-5,13-dienoic acid (referred to alternatively as "$PGF_{2\beta}$"); and $9\alpha,11\alpha,15$-trihydroxy-prosta-5,13-17-trienoic acid (referred to alternatively as "$PGF_{3\alpha}$").

Physiological activity of specific natural prostaglandin compounds may be the same, different in degree or differ from the physiological activity of other specific natural prostaglandins. It would appear, however, that they all share a common property in not being continually produced and released by the mammalian tissues of origin. Instead, the prostaglandins appear to be spontaneously synthesized in situ (biosynthesis being equivalent to release) in response to certain stimuli or "trigger" mechanisms. The naturally occuring prostaglandins generally exhibit an extremely short biological half-life and current knowledge indicates that there is no storage of prostaglandins by body tissues or fluids, with the possible exception of seminal fluids. It has been suggested that the trigger or stimulus for endogenous prostaglandin synthesis is associated with trauma of cellular membranes. Such trauma may occur through physical or chemical activity. For example, in the normal mammal carrying a fetus, circulating blood and amniotic fluids do not contain significant amounts of the prostaglandins $PGE_2$ and $PGF_{2\alpha}$ until birth is imminent. At that time the levels of $PGE_2$ and $PGF_{2\alpha}$ produced by placental and uterine tissues rise substantially. The suggested function of the prostaglandins at this stage of pregnancy is to stimulate uterine contractions, i.e., labor induction. As another example, injury to mammalian epidermal tissue triggers in situ synthesis of $PGE_2$ at the site of injury. $PGE_2$ is known to promote and accelerate healing of epidermal wounds (see for example U.S. Pat. No. 3,711,515, at Column 5, lines 1–11).

We have discovered that the quantity of prostaglandins produced endogenously by a mammal following the stimulation of biosynthesis will be greatly enhanced, e.g., by from 5 to 10 percent to several times normal production, when certain 1-pyridylalkyl-3-naphthyl-2-(thio)ureas have been systemically administered to the mammal prior to the stimulation of biosynthesis by normal trigger mechanisms.

Prior to our invention, there was a suggestion that thrombin caused an increase in the production levels of $PGE_2$ and $PGF_{2\alpha}$ in mammalian blood platelets, (Smith, et al., Nature New Biol., 231, 235).

Prior to our invention, the treatment of clinical conditions responsive to the presence of prostaglandins had been limited to the administration of prostaglandins from exogenous sources. The method of our invention has a number of advantages over the administration of exogenous prostaglandins. For example, as mentioned above, the biological half-life of the naturally occuring prostaglandins is extremely short. Illustratively, it has been reported that after about twenty minutes, 500 μg. of $PGF_{2\alpha}$, administered intravenously to an adult human, cannot be detected in the body. Therefore to treat clinical conditions such as epidermal injury with exogenous sources of prostaglandins, it is necessary to employ a continuous administration of the desired prostaglandin over a prolonged period of time. By our method, therapeutic levels of prostaglandins are delivered at the "target site" or site of injury with maximum efficiency. Sustained high levels of prostaglandins are observed for several hours following treatment according to our method thus eliminating the need for continuous exogenous prostaglandin administration over longer periods of time. In addition, the systemic administration of exogenous prostaglandins delivers the prostaglandin to organs and tissues other than those at the desired "target site". This may result in undesirable responses or "side-effects". By the method of our invention, therapeutic levels of natural prostaglandins are produced at the target site, i.e., at the point of epidermal injury or at the site of synthesis. This reduces the likelihood of responses in remotely located tissues, minimizing side effects.

Prior hereto, 1-(1-naphthyl)-3-(4-pyridylmethyl)-urea; 1-(2-naphthyl)-3-(4-pyridylmethyl)urea; 1-(1-naphthyl)-3-[3-chloro-(4-pyridylmethyl)]urea; 1-(2-naphthyl)-3-[3-chloro-(4-pyridylmethyl)]urea and 1-(2-naphthyl)-3-ethyl-3-(4-pyridylmethyl)-2-thiourea were known; see Novikov, Khim. Geterotsikl Soedin, (1), 115–6, (1968).

SUMMARY OF THE INVENTION

The invention comprises a method of increasing the production of endogenous prostaglandins by a mammal which comprises administering to said mammal an effective amount of a compound selected from those of formula:

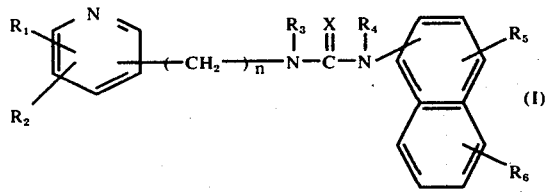

pyridyl N-oxides thereof and pharmaceutically acceptable acid addition salts thereof wherein $R_1$ and $R_2$ are each selected from hydrogen, halogen, hydrocarbyl of 1 to 6 carbon atoms, inclusive, alkoxy, alkylthio, nitro, amino, alkylamino, dialkylamino, acylamino and trihalomethyl; $R_3$ and $R_4$ are each selected from hydrogen, hydrocarbyl, and aryl substituted with a member selected from the group consisting of halogen, nitro, lower alkoxy, and hydrocarbyl; $R_5$ and $R_6$ are each selected from hydrogen, halogen, hydrocarbyl, halogen-substituted hydrocarbyl, nitro, cyano, amino, acylamino, alkylamino, dialkylamino, alkylthio, arylthio, alkoxy and aryloxy; X is selected from oxygen and sulfur; and n is an integer of from 1 to 2, inclusive.

Preferred for carrying out the method of the invention are those compounds (I) having the more specific formula:

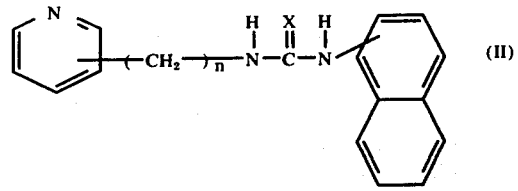

wherein n and X are as defined above, and the pyridyl N-oxides thereof and the pharmaceutically acceptable acid addition salts thereof. Most preferred are those compounds (II wherein n is the integer 1.

The invention also comprises novel compounds within the scope of formula (I) and having the formula (I) provided that when $R_1$, $R_2$, $R_4$, $R_5$ and $R_6$ are each hydrogen and X is sulfur, then $R_3$ is selected from hydrogen, cycloalkyl, aralkyl, aryl and aryl substituted with a group selected from halogen, nitro, lower alkoxy, and hydrocarbyl; and further provided that when $R_1$ and $R_2$ are each selected from hydrogen and halogen and $R_4$, $R_5$ and $R_6$ are each hydrogen and X is oxygen, then $R_3$ is selected from lower alkyl, cycloalkyl, aryl, aralkyl and aryl substituted with a group selected from halogen, nitro, lower alkoxy and hydrocarbyl.

Preferred novel compounds for use in the method of the invention are those of the more specific formula:

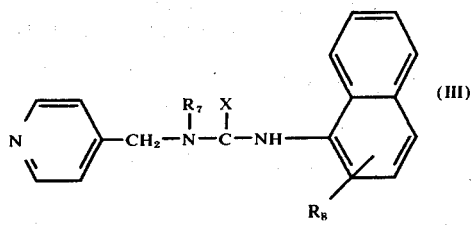

and the pharmaceutically acceptable acid addition salts thereof wherein X is an defined above; $R_7$ is selected from hydrogen and lower alkyl; $R_8$ is selected from halogen, lower alkyl, alkoxy of one to four carbon atoms inclusive, and alkylthio of one to four carbon atoms, inclusive.

The term "halogen" is used herein in its conventional sense as embracive of chlorine, bromine, fluorine and iodine and the term "halo" means chloro, bromo, fluoro and iodo, respectively.

The term "hydrocarbyl" is used throughout the specification and claims as meaning the monovalent moiety obtained by removal of a hydrogen atom from a parent hydrocarbon, which latter contains 1 to 12 carbon atoms. Illustrative of such moieties are alkyl of 1 to 12 carbon atoms, inclusive, such as methyl, ethyl, propyl, butyl, pentyl, hexyl, heptyl, octyl, nonyl, decyl, undecyl, dodecyl and isomeric forms thereof; cycloalkyl of 3 or 8 carbon atoms, inclusive, such as cyclopropyl, cyclobutyl, cyclopentyl, cyclohexyl, cycloheptyl, cyclooctyl and the like; alkenyl of 2 to 12 carbon atoms, inclusive, such as vinyl, allyl, butenyl, pentenyl, hexenyl, heptenyl, octenyl, nonenyl, decenyl, undecenyl, dodecenyl and isomeric forms thereof; aryl of 6 to 12 carbon atoms, inclusive, such as phenyl, tolyl, xylyl, naphthyl, biphenylyl and the like, aralkyl of 7 to 12 carbon atoms, inclusive, such as benzyl, phenethyl, phenpropyl, phenbutyl, phenpentyl, phenhexyl and the like.

The terms alkyl, aryl, cycloalkyl aralkyl, and alkenyl as used in this specification and claims are defined as in the above paragraph.

The term "halogen-substituted hydrocarbyl" means hydrocarbyl as defined above wherein one or more hydrogen atoms have been replaced with a halogen atom as defined above. Illustrative of halogen-substituted hydrocarbyl are trichloromethyl, bromocyclobutyl, 1,2-diiodovinyl, chlorophenyl, p-chlorobenzyl and the like.

The term "alkoxy" is used herein to mean the monovalent moiety of the formula:

— O — alkyl wherein alkyl is as described above. Illustrative of alkoxy are methoxy, ethoxy, butoxy, pentyloxy, heptyloxy, decyloxy, dodecyloxy, and the like.

The term "aryloxy" is used herein to mean the monovalent moiety of formula:

aryl — O — wherein aryl is as defined above. Illustrative or aryloxy are phenoxy, naphthoxy and the like.

The term "alkylthio" means the monovalent moiety of formula:

alkyl — S — wherein alkyl is as defined above. Representative of alkylthio are methylthio, pentylthio, dodecylthio and the like.

The term "arylthio" as used herein means the monovalent moiety of formula:

aryl — S — wherein aryl is as defined above. Illustrative of arylthio are phenylthio, naphthylthio and the like.

The term "alkylamino" is used herein to mean an amino group wherein one hydrogen has been replaced with an alkyl group as previously defined. Illustrative of alkylamino are methylamino, butylamino, dodecylamino and the like.

The term "dialkylamino" is used to mean an amino group wherein both hydrogen atoms have been replaced with alkyl groups as defined above. Illustrative of dialkylamino are groups such as dimethylamino, ethylhexylamino, didodecylamino and the like.

The term "acylamino" as used herein means the monovalent moiety of formula:

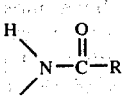

wherein R is alkyl as previously defined.

The term "lower alkyl" means alkyl as previously described having 1 to 4 carbon atoms, inclusive, and the term "lower alkoxy" means alkoxy as defined above having 1 to 4 carbon atoms, inclusive.

One skilled in the art will appreciate a variety of useful procedures which may be carried out by using the method of our invention. For example, natural prostaglandins are sought after for biological studies and as therapeutics in the treatment of mammals for a variety of clinical conditions. The extraction and recovery of natural prostaglandins from animal tissues such as lung tissue, male accessory genital glands and the like from sacrificed animals is a costly procedure and any improvement of yields is a significantly valuable commercial factor. By the method of our invention, effective amounts of compounds of the formula (I) are administered to the natural prostaglandin producing animal within a period of from 1 to about 6 hours prior to sacrifice. This results in enhanced yields of prostaglandins recovered by the conventional and known methods of extraction.

By the method of our invention, mammal treatment procedures for a variety of clinical conditions responsive to prostaglandins are improved. More specifically, those clinical conditions which are related to a prostaglandin deficiency or which respond to enhanced levels of prostaglandins and in which there is an operative trigger mechanism for stimulation of prostaglandin production are advantageously responsive to the method of our invention. Illustratively, some 13 different prostaglandins, representing all four prostaglandin families, are found in mammalian seminal fluids. A correlation exists between low prostaglandin levels (particularly of the PGE family) in seminal fluids and male infertility; see for example, "The Prostaglandins", Karim, Medical and Technical Pub. Co. Ltd., Oxford (1972) pp. 134-6. In those instances wherein seminal fluid prostaglandins are produced by the mammal, but in low quantity, production levels are raised by the method of our invention. Thus, the method of our invention provides a method of treating mammalian male infertility which comprises administering to said male an effective amount of a compound (I) or a pyridyl N-oxide or a pharmaceutically acceptable acid addition salt thereof.

To further illustrate the use of the method of our invention, it is known that the prostaglandin $PGE_2$ is produced at the site of epidermal injury in a mammal [see for example Anggard, et al., Alza Conference on Prostaglandins in Cellular Biology, Edited by Ramwell and Pharriss, Plenum Press, N.Y., N.Y. (1972) at page 269]. The generally accepted role of $PGE_2$ at the site of injury following, for example, burns, abrasions, surgery, penetration wounds and like epidermal injuries is to stimulate epidermal cell proliferation and keratin formation, thereby accelerating wound healing. It should be further noted that the term epidermal injury is broad enough in this context to include skin conditions such as psoriasis wherein the $PGE_2$ stimulates production of cyclic AMP which additionally aids in overcoming the effects of the condition. By using the method of our invention, higher levels of $PGE_2$ are obtained over long periods of time to accelerate the healing process. Thus, a preferred embodiment of the method of our invention comprises a method of promoting the healing of epidermal injuries in a mammal which comprises administering to said mammal an effective amount of a compound selected from those of the formula (I), pyridyl N-oxides thereof and pharmaceutically acceptable acid addition salts thereof. Surprisingly, although $PGE_2$ is a known mediary in the inflammatory process, the method of our invention so employed does not produce a significant increase in the manifestations generally associated with inflammation, such as pain, edema, swelling and like inflammatory manifestations.

In another use, the method of our invention is employed advantageously to prevent or control atonic uterine bleeding $PGE_2$ and $PGF_2$ are both produced by the endometrium and blood platelets (upon aggregation). In situations of post-partum hemmorrhage due to an atonal uterus, the elevation of $PGE_2$ and $PGF_2$ production by platelets at the site of bleeding provides therapeutic levels of the two prostaglandins sufficient to render tone to the uterine muscle, thus causing sustained contraction of the uterus and controlling hemorrhage. The method of our invention therefore includes as an embodiment, the prevention and control of atonic uterine hemmorrhage in a mammal which comprises administering to the mammal an effective amount of a compound selected from those of formula (I), pyridyl N-oxides thereof and pharmaceutically acceptable acid addition salts thereof. Administration of the compound (I) its N-oxides or its salts in this particular use is advantageously carried out during a period of from 1 to about 6 hours before an anticipated hemorrhage to prevent the same, or immediately following the start of hemorrhage. In the latter instance, control of bleeding generally occurs within from 1 to about 3 hours of administration.

As mentioned above, $PGF_{2\alpha}$ and $PGE_2$ are both produced by the mammalian blood platelet upon stimulation of synthesis by cell aggregation. Build-up of $PGF_{2\alpha}$ and $PGE_2$ levels at the site of platelet aggregation are associated with inhibition of further platelet aggregation, thereby terminating the continued development of thrombi. By the method of our invention, one may terminate the development of thrombi earlier and more rapidly through enhanced levels of $PGF_{2\alpha}$ and $PGE_2$ production. This is particularly useful in the treatment and prevention of myocardial infarcts, postoperative thrombosis, atherosclerosis, arteriosclerosis and like clinical conditions where the development of a thrombus is undesired. Thus, another embodiment of our invention comprises a method of controlling the development of a thrombus in a mammal which comprises administering an effective amount of a compound selected from those of formula (I), pyridyl N-oxides thereof and pharmaceutically acceptable acid addition salts thereof, to said mammal.

DETAILED DESCRIPTION OF THE INVENTION

The compounds (I), pyridyl N-oxides thereof and pharmaceutically acceptable acid addition salts thereof are administered to the mammal systemically and topically. Illustrative of the systemic methods of administration are oral and parenteral. However, a systemic effect can be achieved through a topical administration, such as a rectal suppository. Preferred modes of administration are oral and parenteral. Topical composition in the form of lotion, cream, etc. can be used for treating conditions such as epidermal injury, for example, psoriasis.

The effective amount administered is that quantity which brings about an increase in the production levels of prostaglandins biosynthesized by the subject mammal. The exact amount administered will depend upon a number of factors such as, for example, the specific compound (I), the N-oxide or salt, species of mammal, age, weight and physical condition of the mammal, route of administration and in the instances wherein a specific clinical condition is being treated by the method of the invention, the nature of the condition. In general, prostaglandin production levels rise in direct proportion to the quantity of the compound (I) administered.

The exact dosage requirement in a given situation may be determined by administration of a trial dose and observation of the prostaglandin production response by blood plasma analysis or by clinical response to the presence of prostaglandins. In general, an effective amount to be administered is within the range of from about 0.1 mg. to about 500 mg. per kilogram of body weight of the recipient mammal and preferably within the range of from about 5 mg. to about 50 mg. per kilogram body weight. In general, the degree of response is related to dose, and higher doses produce faster and more complete clinical responses. In most instances, a single administration of a compound (I), pyridyl N-oxides thereof or pharmaceutically acceptable acid addition salt thereof will effect the desired response and bring about the result desired. In cases such as the treatment of epidermal injuries however, it may be desirable to repeat the administrations several times. In instances of repeated administration, we have noted a decrease in degree of prostaglandin production response upon administrations subsequent to the first unless there is a resting period between administrations. Resting periods of from about 12 to about 24 hours between administrations assure the highest prostaglandin production for a given dosage of the compounds (I), their N-oxides and pharmaceutically acceptable acid addition salts.

Although all mammalian tissues capable of producing prostaglandins are responsive to the method of our invention the most advantageous response is obtained from circulating blood platelets which produce $PGE_2$ and $PGF_{2\alpha}$. The platelets produce larger quantities of these prostaglandins and serve to meet therapeutic needs as described above most readily and conveniently. The method of our invention is particularly advantageous in stimulating high yields of $PGF_2$ from the producing blood platelets.

Illustrative of the compounds of formula (I) are 1-(1-naphthyl)-3-(4-pyridylmethyl)urea; 1-(2-naphthyl)-3-(4-pyridylmethyl)urea; 1-(1-naphthyl)-3-[3-chloro(4-pyridylmethyl)]urea; 1-(2-naphthyl)-3-[3-chloro(4-pyridylmethyl)] and 1-(2-naphthyl)-3-ethyl-3-(4-pyridylmethyl)-2-thiourea.

The compounds (I) are readily prepared by a variety of methods well known in the art. For example, those compounds of formula (I) wherein $R_4$ is hydrogen and $R_5$ and $R_6$ are other than amino or alkylamino, i.e., a compound of formula (VI) may be prepared by reacting equimolar proportions of an appropriate naphthyl(thio)isocyanate (V) with an appropriate aminoalkylpyridine (IV) according to the schematic formula:

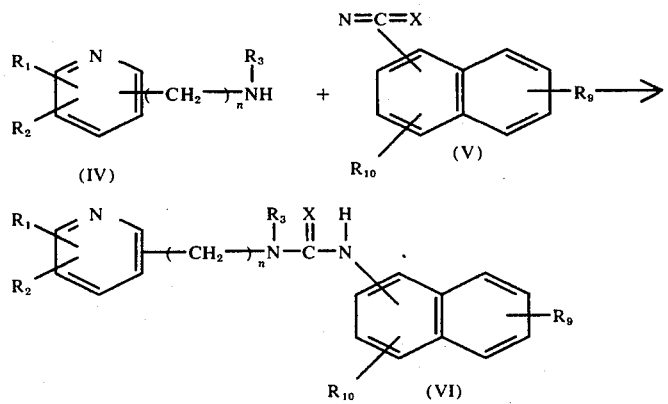

wherein $R_1$, $R_2$, $R_3$, X and n are as previously defined; $R_9$ and $R_{10}$ are each selected from hydrogen, halogen, hydrocarbyl, halogen-substituted hydrocarbyl, nitro, cyano, dialkylamino, acylamino, alkylthio, arylthio, alkoxy and aryloxy. The reaction illustrated above proceeds satisfactorily in the presence of an inert organic solvent such as tetrahydrofuran, dioxane, benzene, pyridine and the like and at temperatures within the range of from about 0° C. to 100° C. Completion of the reaction is readily ascertained by conventional methods such as by infra-red spectral analyses which shows the disappearance of the starting reactant (V). Upon completion of the reaction, the desired product compounds (VI) are separated by conventional means such as by filtration, evaporation of solvent, crystallization and like techniques. Complete details for carrying out the above-described reaction are disclosed in a number of references; see for example A. Shoeb et al., Indian J. Chem. 5, 145 (1967).

The aminoalkylpyridines of formula (IV) are generally well known and may be prepared by a variety of methods. A convenient method of preparing the aminoalkylpyridines (IV) wherein $R_1$ and $R_2$ are other than acylamino groups is by reduction of the corresponding amide compounds of formula:

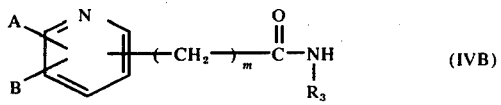

(IVB)

wherein $m$ is an integer of from 0 to 1 $R_3$ is as defined above; A and B are each selected from hydrogen, halogen, hydrocarbyl of 1 to 6 carbons, inclusive, alkoxy, alkylthio, nitro, amino, alkylamino, dialkylamino and trihalomethyl. The methods of reduction are well known, see for example, Tarbell et al., J. Am. Chem. Soc., 72, 2657 (1950); Uffer et al., Helv. Chim. Acta., 31, 1397 (1948); and Brown, Org. Reactions, Vol. 6, J. Wiley and Sons, N.Y., N.Y., (1951), page 469.

Representative of the compounds (IVB) are 2-chloro-6-ethylthioisonicotinamide, N-butyl-2-ethylthioisonicotinamide, N-benzyl-4-pyridylacetamide, 2-pyridineacetanilide, 4′-phenoxynicotinanilide, 2′-phenylnicotinanilide, 5′-methyl-4′-nitro-o-picolinonisidide, 4′-cyclohexylnicotinanilide, N-1-naphthylisonicotinamide, 4′-chloroisonicotinanilide, p-isonicotinanisidine, 2′-chloro-4′-nitropicolinanilide and 2′,5′-diethoxy-4′-nitropicolinanilide, N-butyl-2,6-dichloroisonicotinamide, 2-chloro-6-methoxy-N-(α-methylphenylethyl)isonicotinamide, N-[3-(o-chlorophenyl)propyl]isonicotinamide, N-cyclopropylisonicotinamide, 2,6-dichloro-N-(cyclopropylmethyl)isonicotinamide, N-(diphenylmethyl)isonicotinamide, N-butyl-6-methylthiopicolinamide, N-cyclohexylpicolinamide, 4,6-dichloropicolinamide, 4-ethoxypicolinamide, 5-ethylthiopicolinanilide, and the like.

An alternative method of preparing the aminoalkylpyridines (IV) wherein $R_3$ is specifically hydrogen and the method for preparing the compounds (IV) wherein $R_1$ or $R_2$ is an acylamino group is that disclosed by Sculley et al., supra, which comprises reducing the corresponding nitrile compounds of formula:

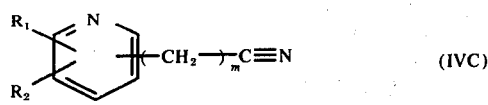

(IVC)

wherein $R_1$, $R_2$ and m are as before defined. Representative of the compounds (IVC) are picolinonitrile, 4-chloropicolinonitrile, 3,6-dichloropicolinonitrile, 4-methylpicolinonitrile, 4,6-dimethylpicolinonitrile, 4-phenylpicolinonitrile, 4-benzylpicolinonitrile, 3-allypicolinonitrile, 4-methoxypicolinonitrile, 2,5-diethoxypicolinonitrile, 4-methylthiopicolinonitrile, 3,5-dinitropicolinonitrile, 3,5-diaminopicolinonitrile, 3-ethylaminopicolinonitrile, 3-diethylaminopicolinonitrile, 4-acetylaminopicolinonitrile, 4-trifluoromethylpicolinonitrile and the like.

Naphthylisocyanates within the formula (V) are generally well known as is their preparation. Those naphthylisocyanates within the scope of the formula (V) are conveniently prepared by phosgenation of the corresponding naphthylamine of formula:

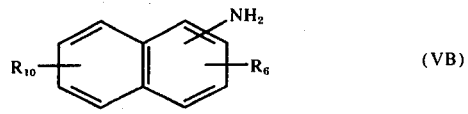

(VB)

wherein $R_9$ and $R_{10}$ are each as defined previously. The methods of phosgenation are well known; see for example Saunders and Frisch, Polyurethanes: Chemistry and Technology; Part I, Chemistry, Interscience Pub. So., N.Y., N.Y. (1962), pp. 17-29.

Illustrative of the naphthylamines (VB) are 2-naphthyl-amine, 4-chloro-2-naphthylamine, 7-chloro-2-naphthylamine, 1,6-dibromo-2-naphthylamine, 4-methyl-2-naphthylamine, 3-phenyl-2-naphthylamine, 3-methyl-5-phenyl-1-naphthylamine, 4,5-dimethyl-2-naphthylamine, 2-allyl-1-naphthylamine, 6-chloro-5-(trifluoromethyl)-1-naphthylamine, 4-bromo-2-(trifluoromethyl)-1-naphthylamine, 5-(trifluoromethyl)-1-naphthylamine, 2-nitro-1-naphthylamine, 6-nitro-2-naphthyl-amine, 2,6-dinitro-1-naphthylamine, 2-chloro-5-nitro-1-naphthylamine, 4-amino-2-naphthonitrile, 5-amino-1-naphthonitrile, 6-amino-2-naphthonitrile, 4-amino-3-nitronaphthonitrile, 1-amino-3-benzyl-naphthonitrile, 4-amino-2-methyl-1-naphthonitrile, 6-amino-1-naphthonitrile, 4-amino-2-methoxy-1-naphthonitrile, 1-amino-3,4-diethyl-6-methoxy-2-naphthonitrile, 2-amino-6,7-demethoxy-1-naphthonitrile, 1-methylthio-2-naphthylamine, 6-methylthio-2-naphthylamine, 4-methylthio-1-naphthylamine, 3-methoxy-1-naphthylamine, 7-methoxy-1-naphthylamine, 4-phenylthio-1-naphthylamine, 1-benzylthio-2-naphthylamine, 2-(p-tolylthio)-1-naphtyl-amine, 2-phenoxy-1-naphthylamine, 5-(p-nitrophenoxy)-1-naphthylamine and the like.

Naphthylisothiocyanates within the scope of the formula (V) are also generally well known and are prepared readily by methods well known in the art. A convenient preparation is described by Dyson, Organic Synthesis, Coll. Vol. I, 2nd Ed., Wiley, N.Y., N.Y., (1946), pg. 165 which comprises thiophosgenation of the corresponding primary amines (VB), supra.

Those compounds (I) wherein $R_3$ is specifically hydrogen and $R_1$ and $R_2$ are other than amino or alkylamino, i.e., compounds of the formula:

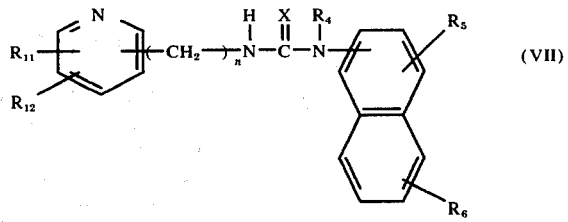

(VII)

wherein $n$, X, $R_4$, $R_5$ and $R_6$ are as defined above and $R_{11}$ and $R_{12}$ are each selected from hydrogen, halogen, hydrocarbyl, halogen-substituted hydrocarbyl, nitro, cyano, dialkylamino, acylamino, alkylthio, arylthio, alkoxy and aryloxy; are prepared by the same general method for preparing the compounds (VI), supra. but by replacing the aminoalkylpyridine (IV) as used therein with the appropriate substituted pyridylalkyl(-thio)isocyanate of formula:

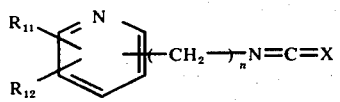

(VIII)

wherein X, n, $R_{11}$ and $R_{12}$ are as defined above, and in conjunction therewith, replacing the naphthyliso(thio)-cyanate (V) as used in the above-described method with an appropriate naphthylamine of formula:

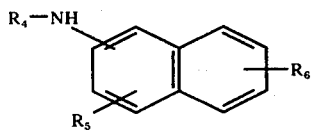

(IX)

wherein $R_4$, $R_5$ and $R_6$ are as defined above.

Pyridylalkylisocyanates of formula (VIII) wherein X is oxygen are conveniently prepared by phosgenation of the corresponding pyridylalkylamine of formula:

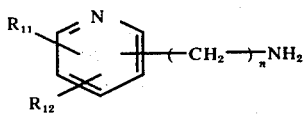

(VIII B)

wherein $R_{11}$, $R_{12}$ and n are as previously defined. The methods of phosgenation have been discussed above; see Saunders et al., supra. Pyridylalkylamines (VIII B) are within the scope of the pyridylalkylamines (IV) discussed above.

Pyridylalkylisothiocyanates within the formula (VIII) are prepared readily by thiophosgenation of the corresponding pyridylalkylamines (VIII B), supra. The thiophosgenation method of Dyson, supra., may be employed for such a synthesis.

Napthylamines of the formula (IX) are also generally well known as illustrated by N-ethyl-2-naphthylamine, N-cyclohexyl-1-naphthylamine, N-phenyl-1-naphthylamine, N-(p-tolyl)-1-naphthylamine, N-benzyl-2-naphthylamine, N-phenethyl-2-naphthylamine, N-(m-fluorophenyl)-2-naphthylamine, N-(2,5-dichlorophenyl)-2-naphthylamine, naphthylamine compounds of the formula (VB), supra. and the like.

Those compounds of formula (I) wherein one or more of the groups $R_1$, $R_2$, $R_5$ and $R_6$ are amino or alkylamino groups are prepared by conventional methods starting with the corresponding compound (I) wherein the appropriate group $R_1$, $R_2$, $R_5$ and/or $R_6$ is a nitro group. The starting appropriate nitro compound is reduced by conventional means such as, for example, the method of Pietra, Ann. Chim. 45, 850 (1955), to obtain the corresponding amine. The amine group may then be converted to an alkylamino group by conventional methods such as by alkylation with an appropriate alkyl halide of the formula:

Alkyl—Y wherein Y is halogen, such as methyl iodide, pentyl iodide, dodecyl iodide and the like; see for example the method of Johnstone et al., J. Chem. Soc., (c), 2223 (1969). When desired compounds (I) wherein $R_1$, $R_2$, $R_5$ and/or $R_6$ may be prepared from the corresponding compounds (I) wherein said groups $R_1$, $R_2$, $R_5$ and $R_6$ are amino groups. The conversion of an amino group to an acylamino group is likewise by conventional methods such as by N-acylation with an appropriate acyl halide of formula

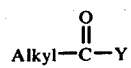

wherein alkyl and Y are as defined above, such as acetyl chloride and the like.

The pyridyl N-oxides of the compounds (I), i.e., compounds of the formula:

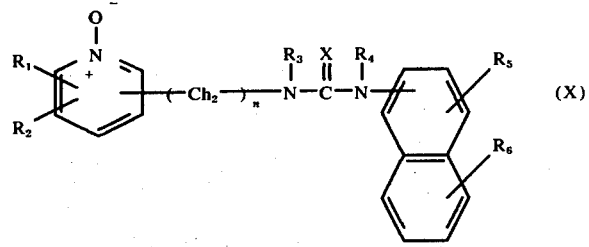

(X)

and the pharmaceutically acceptable acid addition salts thereof wherein $R_1$, $R_2$, $R_3$, $R_4$, $R_6$, X and n have the meanings previously ascribed to them are also novel compounds and are useful for the same purposes and in the same manner as the non-oxides of formula (I).

The pyridyl N-oxides (X) are prepared by N-oxidation of the corresponding compound (I). Such oxidations are well known, and are generally carried out by reacting the compound (I) with an excess molar proportion of an oxidizing agent such as hydrogen peroxide. See for example the procedure disclosed in E. Ochia, Aromatic Amino Oxides, Elsevier Pub. Co., N.Y., N.Y. pg. 25, (1967).

The pharmaceutically acceptable acid addition salts of the compounds (I) and compounds (X) may be used for the same purposes as the corresponding free bases compounds, and in the same manner. They are readily prepared by reacting the free base with a stoichiometric proportion of an appropriate acid. The method is well known to those skilled in the art and may be carried out in aqueous or non-aqueous media such as ethanol, ether, ethyl acetate and the like. Illustrative of pharmaceutically acceptable acid addition salts are those formed upon reaction of the free base compound (I) or compound (X) with hydrochloric acid, hydrobromic acid, sulfuric acid, phosphoric acid, acetic acid, lactic acid, citric acid, succinic acid, benzoic acid, salicylic acid, pamoic acid, cyclohexanesulfamic acid and the like.

This invention relates also to pharmaceutical dosage unit forms for systemic and topical administration which are useful in improving the production of endogenous prostaglandins by mammals, including humans. Preferred are those forms for oral and parenteral administration. The term "dosage unit form" as used in this specification and in the claims refers to physically discrete units suitable as unitary dosages for mammalian subjects, each unit containing a predetermined quantity of the essential active ingredient, i.e., a compound selected from those of formula (X); and compounds of the formula (I) provided that when $R_1$, $R_2$, $R_4$, $R_5$ and $R_6$ are each hydrogen and X is sulfur, then $R_3$ is selected from hydrogen, cycloalkyl, aryl, aralkyl and aryl substituted with a group selected from halogen, nitro, lower alkoxy and hydrocarbyl; from one to six carbon atoms, inclusive and further provided that when $R_1$ and $R_2$ are each selected from hydrogen and halogen and $R_4$, $R_5$ and $R_6$ are each hydrogen and X is oxygen, then $R_3$ is selected from lower alkyl, lower cycloalkyl, aryl, aralkyl and aryl-substituted with a group selected from halogen, nitro, lower alkoxy and hydrocarbyl from one to six carbon atoms, inclusive, or pharmaceutically acceptable acid addition salts thereof, calculated to produce the desired effect in combination with the required pharmaceutical means which adapt said ingredient for systemic administration. Examples of dosage unit forms in accordance with this invention are tablets, capsules, orally administered liquid preparations in liquid vehicles, sterile preparations in liquid vehicles, sterile preparations in liquid vehicles for intramuscular and intravenous administration, rectal suppositories for topical application, sterile dry preparations for the extemporaneous preparation of sterile injectable preparations in a liquid vehicle and lotions, creams, aerosols, ointments, pastes, jellies, sprays and the like. Solid diluents or carriers for the solid oral pharmaceutical dosage unit forms are selected from the group consisting of lipids, carbohydrates, proteins and mineral solids, for example starch, sucrose, kaolin, dicalcium phosphate, gelatin, acacia, corn syrup, corn starch, talc and the like. Capsules, both hard and soft, are formulated with conventional diluents and excipients, for example edible oils, talc, calcium carbonate, calcium stearate and the like. Liquid preparations for oral administration are prepared in water or aqueous solutions which advantageously contain suspending agents, such as for example carboxymethylcellulose, acacia, polyvinyl pyrrolidone, polyvinyl alcohol and the like. In the instance of injectable forms, they must be sterile and must be fluid to the extent that easy syringeability exists. Such preparations must be stable under the conditions of manufacture and storage and ordinarily contain in addition to the basic solvent or suspending liquid, preservatives in the nature of bactericidal and fungicidal agents, for example parabens, chlorobutanol, benzyl alcohol, phenol, thimerosal and the like. In many cases it is preferable to include isotonic agents, for example sugars or sodium chloride. Carriers and vehicles include vegetable oils, ethanol and polyols, for example glycerol, propylene glycol, liquid polyethylene glycol and the like. Any solid preparations for subsequent extemporaneous preparation of sterile injectable preparations are sterilized, preferably by exposure to a sterilizing gas such as for example, ethylene oxide. The aforesaid carriers, vehicles, diluents, excipients, preservatives, isotonic agents and the like constitute the pharmaceutical means which adapt the preparations for systemic administration.

For topical use, this compound can be formulated in a pharmaceutical carrier suitable for application to affected areas of the skin, eyes, ears or mucous membranes. Accordingly, the compositions, of this invention include those pharmaceutical forms in which the medication is applied externally for direct contact with the surface to be treated. Conventional pharmaceutical forms for this purpose include ointments, creams, lotions, solutions, suspensions, pastes, jellies, sprays and aerosols (e.g. for oral or nasal use or on the skin), drops (e.g. for use in the eyes or ears), powders (e.g. for use on the skin) and the like. In preparing the desired topical formulations of the novel compound of this invention, various additives, diluents and adjuvants can be utilized. These illustratively include water, surfactants (e.g., polysorbate 80 and polyoxyethylene sorbitan monostearate), emulsifiers (e.g., glyceryl monostearatediethylaminoethyl alkyl amide phosphate, isopropyl myristate and cetyl alcohol; alcohols (e.g., ethanol and isopropanol), lower alkyl diols (e.g. 1,3-butanediol, 2,3-butanediol, 1,2-propanediol, 1,3-propanediol), glycols (e.g., propylenen glycol, glycerol, sorbitol), ointment-type bases (e.g., spermaceti, Carbowaxes, beeswax, petrolatum, lanolin), higher fatty acids and alcohols (e.g., stearic acid, stearyl alcohol, cetyl alcohol, palmitic acid), liquid paraffin and vegetable oils (e.g., peanut oil, caster oil), preservatives such as sorbic acid, parabens, chlorocresol, benzalkonium chloride, and solid diluents (e.g., lactose, starch bentonite, talc).

A rectal suppository can be employed to deliver the active compound where the mammal cannot be treated conveniently by means of other dosage forms, such as orally, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 gm.

The pharmaceuitcal dosage unit forms are prepared in accordance with the preceding general description to provide from about 10 to about 1500 mg. of the essential active ingredient per dosage unit form preferred of from about 100 to about 1000 mg. For topical administration, the essential active ingredient is from about 1 to about 10 weight percent.

The following examples describe the manner and process of making and using the invention, and set forth the best mode contemplated by the inventors of carrying out the invention but are not to be construed as limiting.

EXAMPLE 1

1-(1-naphthyl)-3-(4-pyridylmethyl)-2-thiourea

An appropriate reaction flask is charged with 3.25 gms. (0.03 mole) or 4-aminomethylpyridine in 100 ml. of tetrahydrofuran and 5.56 gms. (0.03 mole) of 1-naphthylisothiocyanate is added with stirring. Upon completion of admixture, the mixture is allowed to stand for 23 hours at ambient temperatures. At the end of this period, the mixture is refluxed for 30 minutes, diluted to a volume of 1 liter with water and allowed to cool to room temperature. Upon cooling, a solid in the mixture is separated, washed with water and dried to give 5.92 gms. (67 percent of theory) of 1-(1-naphthyl)-3-(4-pyridylmethyl)-2-thiourea in the form of pale yellow granules, M. P. 119.5° C.

Similarly, following the above procedure but replacing the 1-naphthylisothiocyanate as used therein with an equal molar proportion of 7-chloro-2-naphthylisothiocyanate, 1-bromo-2-naphthylisothiocyanate, 4- methyl-2-naphthylisothiocyanate, 3-methyl-5-phenyl-1-naphthylisothiocyanate, 2-allyl-1-naphthylisothiocyanate, 1,6-dibromo-2-naphthylisothiocyanate, 6-chloro-5-trifluoromethyl-1-naphthylisothiocyanate, 4-bromo-2-trifluoromethyl-1-naphthylisothiocyanate, 5-trifluoromethyl-1-naphthylisothiocyanate, 2-nitro-1-naphthylisothiocyanate, 6-nitro-2-naphthylisothiocyanate, 3-cyano-1-naphthylisothiocyanate, 1-methylthio-2-naphthylisothiocyanate, 6-methylthio-2-naphthylisothiocyanate, 3-methoxy-1-naphthylisothiocyanate, 7-methoxy-1-naphthylisothiocyanate, 4-phenylthio-1-naphthylisothiocyanate, 4-diethylamino-1-naphthylisothiocyanate, 1-benzylthio-1-naphthylisothiocyanate and 2-phenoxy-1-naphthylisothiocyanate respectively, [all of which are prepared by thiophosgenation of the corresponding amine of formula (VB) (See Dyson, supra.)], there is obtained 1-(7-chloro-2-naphthyl)-;
1-(7-bromo-2-naphthyl)-;
1-(4-methyl-2-naphthyl)-;
1-(3-methyl-5-phenyl-1-naphthyl)-;
1-(2-allyl-1-naphthyl)-;
1-(7-chloro-2-naphthyl)-;
1-(1,6-dibromo-2-naphthyl)-;
1-(6-chloro-5-trifluoromethyl-1-naphthyl)-;
1-(4-bromo-2-trifluoromethyl-1-naphthyl)-;
1-(5-trifluoromethyl-1-naphthyl)-;
1-(2-nitro-1-naphthyl)-;
1-(6-nitro-2-naphthyl)-;
1-(3-cyano-1-naphthyl)-;
1-(1-methylthio-2-naphthyl)-;
1-(6-methylthio-2-naphthyl)-;
1-(3-methoxy-1-naphthyl)-;
1-(7-methoxy-1-naphthyl)-;
1-(4-phenylthio-1-naphthyl)-;
1-(4-diethylamino-1-naphthyl)-;
1-(1-benzylthio-2-naphthyl)-;
1-(2-phenoxy-1-naphthyl)-3-(4-pyridylmethyl)-2-thiourea,
respectively.

EXAMPLE 2

1-(2-naphthyl)-3-(4-pyridylmethyl)-2-thiourea

Following the procedure of Example 1, supra., but replacing the 1-naphthylisothiocyanate as used therein with an equal molar proportion of 2-naphthylisothiocyanate there is obtained 7.45 gms. (85 percent of theory) of 1-(2-naphthyl)-3-(4-pyridylmethyl)-2-thiourea in the form of tan granules, M. P. 174.0° C.

Similarly, following the above procedure but replacing the 4-aminomethylpyridine as used therein with an equal molar proportion of 2-aminomethyl-6-methylpyridine, 2-(2-aminoethyl)-5-ethylpyridine, 3-amino-5-(aminomethyl)-2-methylpyridine, 2-(aminomethyl)-3-chloropyridine, 2-(aminomethyl)-4-phenylpyridine, 2-(aminomethyl)-4-benzylpyridine, 2-(aminomethyl)-4-methoxypyridine, 2-(aminomethyl)-4-methyl-thiopyridine, 2-(aminomethyl)-3-nitropyridine 2-(aminomethyl)-3-ethylaminopyridine, 2-(aminomethyl)-3-diethylaminopyridine, 2-(aminomethyl-4-acetylaminopyridine and 2-(aminomethyl)-4-trifluoromethylpyridine, respectively, all of which may be prepared by reduction of the corresponding nitrile of formula (IVC) (method of Sculley et al.), supra., there is obtained 1-(2-naphthyl)-3-[2-(6-methylpyridylmethyl)]-2-thiourea,
1-(2-naphthyl)-3-[2-(5-ethylpyridylmethyl)]-2-thiourea,
1-(2-naphthyl)-3-[5-(3-amino-2-methylpyridylmethyl)]-2-thiourea,
1-(2-naphthyl)-3-[2-(3-chloropyridylmethyl)]-2-thiourea,
1-(2-naphthyl)-3-[2-(4-phenylpyridylmethyl)]-2-thiourea,
1-(2-naphthyl)-3-[2-(4-benzylpyridylmethyl)]-2-thiourea,
1-(2-naphthyl)-3-[2-(4-methoxypyridylmethyl)]-2-thiourea,
1-(2-naphthyl)-3-[2-(4-methylthiopyridylmethyl)]-2-thiourea,
1-(2-naphthyl)-3-[2-(3-nitropyridylmethyl)]-2-thiourea,
1-(2-naphthyl)-3-[2-(3-ethylaminopyridylmethyl)]-2-thiourea,
1-(2-naphthyl)-3-[2-(3-diethylaminopyridylmethyl)]-2-thiourea,
1-(2-naphthyl)-3-[2-(4-acetylaminopyridylmethyl)]-2-thiourea, and
1-(2-naphthyl)-3-[2-(4-trifluoromethylpyridylmethyl)]-2-thiourea, respectively.

EXAMPLE 3

1-(2-naphthyl)-3-(2-pyridylmethyl)-2-thiourea

Following the procedure of Example 2, supra., but replacing the 4-aminomethylpyridine as used therein with an equal molar proportion of 2-aminomethylpyridine there is obtained 7.43 gms. (85 percent of theory) of 1-(2-naphthyl)-3-(2-pyridylmethyl-2-thiourea in the form of fine white needles, M. P. 159.6° C.

EXAMPLE 4

1-(1-naphthyl)-3-(2-pyridylmethyl)-2-thiourea

Following the procedure of Example 1, supra., but replacing the 4-aminomethylpyridine as used therein with an equal molar proportion of 2-aminomethylpyridine there is obtained 7.68 gms. (87 percent of theory) of 1-(1-naphthyl)-3-(2-pyridylmethyl)-2-thiourea in the form of pale yellow crystals, M. P. 155.3° C.

EXAMPLE 5

1-(1-naphthyl)-3-(3-pyridylmethyl)-2-thiourea

Following the procedure of Example 4, supra., but increasing the proportion of 1-naphthylisothiocyanate as used therein to 7.41 gms. (0.04 mole) and replacing the 2-aminomethylpyridine as used therein with 4.33 gms. (0.04 mole) of 3-aminomethylpyridine there is obtained 11.31 gms. (96 percent of theory) of 1-(1-naphthyl)-3-(3-pyridylmethyl)-2-thiourea in the form of colorless crystals, M. P. 193.6° C.

EXAMPLE 6

1-(2-naphthyl)-3-(3-pyridylmethyl)-2-thiourea

Following the procedure of Example 5, supra., but replacing the 1-naphthylisothiocyanate as used therein with an equal molar proportion of 2-naphthylisothiocyanate there is obtained 10.79 gms. (92 percent of theory) of 1-(2-naphthyl)-3-(3-pyridylmethyl)-2-thiourea in the form of cream colored crystals, M. P. 178.5° C.

EXAMPLE 7

1-methyl-3-(1-naphthyl)-1-(2-pyridylethyl)urea

An appropriate reaction vessel is charged with 10.2 gms. (0.075 mole) of 2-methylaminoethylpyridine in 100 ml. of tetrahydrofuran and 12.7 gms. (0.075 mole) of 1-naphthylisocyanate is added with stirring. Upon completion of the addition the resulting mixture is allowed to stand at room temperature for 23 hours. At the end of this period, the mixture is refluxed for 30 minutes, diluted to a volume of 1 liter with water and cooled to room temperature. The solids are separated, washed with water and dried to give 18.08 gms. (79 percent of theory) of 1-methyl-3-(1-naphthyl)-1-(2-pyridylethyl)urea in the form of light yellow crystals, M. P. 104.7° C.

Similarly, following the above procedure but replacing the 1-naphthylisocyanate as used therein with an equal molar proportion of 7-chloro-2-naphthylisocyanate, 1-bromo-2-naphthylisocyanate, 4-methyl-2-naphthylisocyanate, 3-methyl-5-phenyl-1-naphthylisocyanate, 2-allyl-1-naphthylisocyanate, 1,6-dibromo-2-naphthylisocyanate, 6-chloro-5-trifluoromethyl-1-naphthylisocyanate, 4-bromo-2-trifluoromethyl-1-naphthylisocyanate, 5-trifluoromethyl-1-naphthylisocyanate, 2-nitro-1-naphthylisocyanate, 6-nitro-2-naphthylisocyanate, 3-cyano-1-naphthylisocyanate, 1-methylthio-2-naphthylisocyanate, 6-methylthio-2-naphthylisocyanate, 3-methoxy-1-naphthylisocyanate, 4-diethylamino-1-naphthylisocyanate, 7-methoxy-1-naphthylisocyanate, 4-phenylthio-1-naphthylisocyanate, 1-benzylthio-2-naphthylisocyanate and 2-phenoxy-1-naphthylisocyanate, respectively [all of which are prepared by phosgenation of the corresponding amine of formula (VB), supra.,] there is obtained 1-(7-chloro-2-naphthyl)-;
1-(1-bromo-2-naphthyl)-;
1-(4-methyl-2-naphthyl)-;
1-(3-methyl-5-phenyl-1-naphthyl)-;
1-(2-allyl-1-naphthyl)-;
1-(1,6-dibromo-1-naphthyl)-;
1-(6-chloro-5-trifluoromethyl-1-naphthyl)-;
1-(4-bromo-2-trifluoromethyl-1-naphthyl)-;
1-(5-trifluoromethyl-1-naphthyl)-;
1-(2-nitro-1-naphthyl)-;
1-(6-nitro-2-naphthyl)-;
1-(3-cyano-1-naphthyl)-;
1-(1-methylthio-2-naphthyl)-;
1-(6-methylthio-2-naphthyl)-;
1-(3-methoxy-1-naphthyl)-;
1-(4-diethylamino-1-naphthyl)-;
1-(7-methoxy-1-naphthyl)-;
1-(4-phenylthio-1-naphthyl)-;
1-(1-benzylthio-2-naphthyl)-;
1-(2-phenoxy-1-naphthyl)-3-(2-pyridylethyl)urea,
respectively.

Similarly, following the above procedure but replacing the 2-methylaminoethylpyridine as used therein with an equal molar proportion of 2-cyclohexylaminomethylpyridine,
2-phenylaminomethylpyridine,
2-benzylaminomethylpyridine,
2-(p-chlorophenylaminomethyl)pyridine,
2-(4-biphenylaminomethyl)pyridine,
2-(3-benzylphenylaminomethyl)pyridine,
2-(p-methoxyphenylaminomethyl)pyridine,
2-(m-toluylaminomethyl)pyridine,
2-(4-nitrophenylaminomethyl)pyridine, respectively all of which may be prepared by reduction of the corresponding amides of formula (IVB), supra. (method of Tarbell et al., supra.), there is obtained 1-cyclohexyl-;
1-phenyl-;
1-benzyl-;
1-(p-chlorophenyl)-;
1-(4-biphenyl)-;
1-(3-benzylphenyl)-;
1-(p-methoxyphenyl)-;
1-(m-toluyl)-; and
1-(4-nitrophenyl)-3-(1-naphthyl)-1-(2-pyridylmethyl)urea,
respectively.

EXAMPLE 8

1-(1-naphthyl)-3-(3-pyridylmethyl)urea-N-oxide

To 10.0 gms. (0.0361 mole) of 1-(1-naphthyl)-3-(3-pyridylmethyl)urea (prepared by reacting 1-naphthylisocyanate with 3-aminomethylpyridine) in 50 ml. of acetic acid there is added 5.6 ml. of 30 percent hydrogen peroxide. After standing for one-half hour at room temperature, the reaction mixture is warmed to a temperature of circa 75° C. for a period of about 6 hours, and then stood overnight at room temperature. Acetic acid is then removed under reduced atmospheric pressure and the residue suspended in water. The suspension is treated with sodium bicarbonate, the solids separated by filtration, washed with water and dried. The dried solid is then dissolved in absolute ethanol and the solution treated with Nuchar and filtered. The filtrate is concentrated to a volume of 100 ml., diluted with 100 ml. of ethyl acetate and chilled. The resulting precipitate is separated and dried to give 6.79 gms. (64 percent of theory) of 1-(1-naphthyl)-3-(3-pyridylmethyl)urea-N-oxide in the form of purple crystals, M. P. 187.9° C.

EXAMPLE 9

1-(1-naphthyl)-3-(4-pyridylmethyl)urea-N-oxide

Following the procedure of Example 8, supra., but replacing the 1-(1-naphthyl)-3-(3-pyridylmethyl)urea as used therein with 8.32 gms. (0.03 mole) of 1-(1-naphthyl)-3-(4-pyridylmethyl)urea (Novikov, supra.) there is obtained 2.5 gms. (29 percent of theory) of 1-(1-naphthyl)-3-(4-pyridylmethyl)urea-N-oxide in the form of brown crystals, M. P. 178.5° C.

Similarly, following the above procedure but replacing the 1-(1-naphthyl)-3-(4-pyridylmethyl)urea with any other compound of the formula (1), such as those prepared in Examples 1-7, supra., the corresponding pyridyl N-oxide of formula (X) is obtained.

EXAMPLE 10

3-Methyl-3-(1-napthyl)-1-(2-pyridylethyl)urea

To 3.14 gm. (0.02 mole) of N-methyl-1-naphthylamine in 75 ml. of tetrahydrofuran there is added 2.96 gm. (0.02 mole) of 2-pyridylethylisocyanate with stirring. After 30 minutes of stirring at ambient temperature, the mixture is refluxed for 1 hour. The solvent is then removed in vacuo and the residue crystallized from alcohol-water (4:1 v/v) to furnish 3-methyl-3-(1-naphthyl)-1-(2-pyridylethyl)urea.

Similarly, following the above procedure but replacing N-methyl-1-naphthylamine as used therein with an equimolar proportion of N-phenyl-1-naphthylamine, N-phenyl-2-naphthylamine and N-benzyl-1-naphthylamine, respectively, there is obtained 3-phenyl-3-(1-naphthyl)-1-(2-pyridylethyl)urea;
3-phenyl-3-(2-naphthyl)-1-(2-pyridylethyl)urea; and
3-benzyl-3-(1-naphthyl)-1-(2-pyridylethyl)urea,
respectively.

EXAMPLE 11

1-(6-amino-2-naphthyl)-3-(4-pyridylmethyl)urea

To a mixture of 9.66 gms. (0.03 mole) of 1-(6-nitro-2-naphthyl)-3-(4-pyridylmethylurea), (Example 1, supra.) 200 ml. of ethanol and 65 ml. of hydrazine hydrate there is added with stirring 0.5 gms. of 5 percent palladium-on-carbon in 50 ml. of ethanol. The resulting mixture is allowed to stand overnight at room temperature and then is refluxed for 2 to 3 hours. The hot reaction mixture is then filtered and the filtrate evaporated to remove solvent. The residue is 1-(6-amino-2-naphthyl)-3-(4-pyridylmethyl)urea.

EXAMPLE 12

1-(6-acetamide-2-naphthyl)-3-(4-pyridylmethyl)urea

To a chilled (circa 0° C.) solution of 2.92 gms. (0.01 mole) of 1-(6-amino-2-naphthyl)-3-(4-pyridylmethyl)urea (Example 11, supra.) in 50 ml. of pyridine there is added 0.8 gms. (0.01 mole) of acetylchloride with stirring. The mixture is stirred for about 2 hours while maintaining the temperature at about 0° C. The resulting reaction mixture is then evaporated in vacuo and the residue suspended in 50 ml. of 10 percent sodium bicarbonate. Solids are separated, washed with water and dried to give 1-(6-acetamide-2-naphthyl)-3-(4-pyridylmethyl)urea.

EXAMPLE 13

1-(6-methylamino-2-naphthyl)-3-(4-pyridylmethyl)urea

To 3.88 gms. (0.04 mole) of 1-(6-trifluoroacetamide)-2-(naphthyl)-3-(4-pyridylmethyl)urea [prepared by reacting 1-(6-amino-2-naphthyl)-3-(4-pyridylmethyl)urea (Example 11, supra.) with trifluoroacetic anhydride (method of Hickinbottom, Reactions of Organic Compounds, Longmans, London, 1963)] in 50 ml. of dry acetone there is added 5.7 gms. (0.04 mole) of methyl iodide. The resulting mixture is warmed and 2.24 gms. (0.04 mole) of potassium hydroxide is added. The reaction mixture is then refluxed for 10 minutes and then solvent is stopped. The residue is taken up in water (50 ml.) and refluxed for 10 minutes. Upon removal of water there is obtained 1-(6-methylamino-2-naphthyl)-3-(4-pyridylmethyl)urea.

EXAMPLE 14

1-(1-naphthyl)-3-(4-pyridylmethyl)urea-hydrochloride

A solution of 2.77 gm. (0.01 mole) of 1-(1-naphthyl)-3-(4-pyridylmethyl)urea and 50 ml. of chloroform is saturated with anhydrous hydrogen chloride. The solution is then evaporated to dryness in vacuo. The residue is crystallized from alcohol Skellysolve B (9:1 v/v) to give 1-(1-naphthyl)-3-(4-pyridylmethyl)urea hydrochloride.

Similarly, repeating the above procedure, but replacing the 1-(1-naphthyl)-3-(4-pyridylmethyl)urea as used therein with any other compound of the formula (I) such as those prepared in Examples 1–13, supra., the corresponding hydrochloride is obtained.

The following examples illustrate the compositions and uses of the compounds of the invention and the method of the invention.

EXAMPLE 15

Tablets

One thousand tablets for oral use, each containing 250 mg. of 1-(1-naphthyl)-3-(4-pyridylmethyl)-2-thioureas as the essential active ingredient are prepared from the following ingredients:

| | |
|---|---|
| essential active ingredient | 250 gms. |
| lactose | 200 gms. |
| microcrystalline cellulose N.F. | 50 gms. |
| starch | 5 gms. |
| magnesium stearate powder | 1 gm. |

The ingredients are thoroughly mixed and slugged. The slugs are broken down by forcing through a screen and the resulting granules are then compressed into tablets.

These tablets are useful in controlling atonic uterine hemorrhage in adult humans when given at a dose of 1 to 3 tablets. High blood levels of $PGF_{2\alpha}$ and $PGE_2$ are observed for from 6 to 8 hours after administration.

The tablets are also useful for treating male mammals for infertility when 1 to 3 tablets are given 3 to 4 times a week.

EXAMPLE 16

Capsules

One thousand two-piece hard gelatin capsules for oral use, each capsule containing 250 mg. of 1-(1-naphthyl)-3-(3-pyridylmethyl)-2-thiourea are prepared from the following ingredients:

| | |
|---|---|
| 1-(1-naphthyl)-3-(3-pyridylmethyl)-2-thiourea | 250 gms. |
| lactose | 200 gms. |
| talc | 25 gms. |
| magnesium stearate | 2 gms. |

The finely powdered materials are mixed thoroughly, then filled into hard gelatin capsules of appropriate size. The capsules are given to adult humans suffering from burns at a dose of 1 to 3 capsules given 3 to 14 times a week, resulting in an acceleration of healing and epidermal proliferation.

EXAMPLE 17

Aqueous Solution

An aqueous oral preparation containing in each teaspoonful (5 ml.) 500 mg. of essential active ingredient is prepared from the following:

| | |
|---|---|
| 1-(1-naphthyl)-3-(4-pyridylmethyl)urea-N-oxide | 500 gms. |
| glycerin | 2000 ml. |
| tragacanth powder | 50 gms. |
| propyl paraben | 3 gms. |
| sucrose | 6.5 gms. |
| orange oil flavor | 5 gms. |
| deionized water q.s. | 5000 ml. |

The above oral preparation may be given to adult humans at a dose of 1 to 4 teaspoons 3 to 14 times weekly to accelerate the healing of epidermal wounds.

EXAMPLE 18

Injectable

A sterile aqueous suspension suitable for intramuscular injection and containing in each milliliter 250 mg. of 1-(2-naphthyl)-3-(3-pyridylmethyl)-2-thiourea is prepared from the following ingredients:

| | |
|---|---|
| 1-(2-naphthyl)-3-(3-pyridylmethyl)-2-thiourea | 250 gms. |
| benzylbenzoate | 200 ml. |
| methylparaben | 1.5 gms. |
| propylparaben | 0.5 gms. |
| cottonseed oil q.s. | 1000 ml. |

The above sterile injectable is useful in controlling the development of thrombi following saphenectomy when given at a dose of 1 to 4 ml. administered intravenously or intramuscularly 2 to 6 hours prior to said saphenectomy.

EXAMPLE 19

Suppository

One thousand suppositories, each weighing 4.0 gms. and containing 500 mg. of 1-(1-naphthyl)-3-(4-pyridylmethyl)-2-thiourea as the essential active ingredient are prepared from the following ingredients:

| | |
|---|---|
| essential active ingredient | 500 gms. |
| propylene glycol | 2000 gms. |
| polyethylene glycol 4000 | 1000 gms. |
| polyethylene glycol 400 | 500 gms. |

The essential active ingredient is added to the propylene glycol and the mixture milled until uniformly dispersed. The polyethylene glycol 4000 is melted and the propylene glycol dispersion added. The suspension is poured into molds and allowed to cool and solidify.

These suppositories are useful for controlling development of thrombi in mammals when given rectally at a dose of 1 suppository 3 to 7 times a week.

EXAMPLE 20

Various compounds of the formula (I) are admixed with water and administered orally to groups of 5 male Carworth rats (weighing 250–275 gms. each) at a dosage of 60 mg. per kilogram of body weight. The rats are prepared by fasting overnight (16 hours) prior to administration. About 3 hours after administration, tails are clipped and the rats bled. 5 ml. of blood is collected in citrated syringes (0.1 ml. of 3.8 percent w/v sodium citrate per ml. of whole blood). The collected blood is centrifuged at 900 RPM for 15 minutes and the platelet rich plasma separated and pooled for each group of 5 rats. For each 1.0 mls. of pooled plasma there is added 0.5 ml. of 0.15M sodium phosphate buffer (pH 7.4). The resulting mixture is allowed to stand at room temperature for 30 minutes and then 0.5 ml. of sodium fluoride (4 mgs./ml. aqueous solution) is added. The mixture is then incubated at 37° C. for sixty minutes, cooled under running tap water and centrifuged at 2500 RPM for 20 minutes. The supernatent solution is separated and analyzed for $PGF_{2\alpha}$ concentration by the method of Kirton et al.; Biochemical and Biophysical Res. Comm., Vol. 47, 903, (1962).

The compounds employed and the results obtained are given in Table I below. Group A does not represent the invention but is a control group of 5 rats which did not receive an administration of a compound (I).

TABLE I

| Group | Compound (I) Administered | Concentration of $PGF_{2\alpha}$ Found (mg./ml.) |
|---|---|---|
| A (control) | None | 33.8 ± 4.2 |
| B | 1-(1-naphthyl)-3-(4-pyridylmethyl)-2-thiourea | 116.0 ± 20.2 |
| C | 1-(2-naphthyl)-3-(4-pyridylmethyl)-2-thiourea | 45.5 ± 1 |
| D | 1-(1-naphthyl)-3-(4-pyridylmethyl)urea | 62.2 ± 4.0 |

Similarly, repeating the above procedure but replacing the compounds of formula (I) as used therein with any other compounds of the formula (I), or of the formula (X) and the pharmaceutically acceptable acid addition salts thereof prepared according to Examples 1–14 supra., similar observations of increased prostaglandin production are made.

A further group of compounds of the invention are those compounds of Formula I wherein $R_1$, $R_5$ and $R_6$ are hydrogen; $R_2$ is selected from the group consisting of hydrogen, alkyl of one to four carbon atoms, inclusive, and halogen; $R_3$ and $R_4$ are the same or different and selected from the group consisting of hydrogen and alkyl of one to four carbon atoms, inclusive; X is oxygen or sulfur; and n is one or two, provided further that when $R_1$, $R_2$ and $R_4$ are hydrogen and X is sulfur, then $R_3$ is hydrogen, and further provided that when $R_2$ is hydrogen or halogen, $R_4$ is hydrogen and X is oxygen, then $R_3$ is alkyl of one to four carbon atoms, inclusive, and still further provided that when a 2-naphthyl is present, the pyridyl ring is other than the 4-position.

The N-oxides of these compounds are also a portion of the invention. These groupings of compounds are used in the same manner as the larger generic groups and are formulated into like pharmaceutical compositions.

The proviso that when the urea moiety is connected to the "two" position of the naphthyl, that is "a 2-naphthyl is present", the pyridyl ring is other than the 4-position applies to all the compound and composition generic claims.

We claim:

1. A compound of the formula

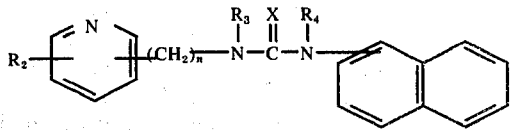

and pharmaceutically acceptable acid addition salts thereof wherein $R_2$ is hydrogen, alkyl of one to four carbon atoms, inclusive, or halogen; $R_3$ and $R_4$ are the same or different and are hydrogen or alkyl of one to four carbon atoms, inclusive; X is oxygen or sulfur; and n is one or two; provided that when $R_2$ and $R_4$ are hydrogen and X is sulfur, then $R_3$ is hydrogen and further provided that when $R_2$ is hydrogen or halogen, $R_4$ is hydrogen and X is oxygen, then $R_3$ is alkyl of one to four carbon atoms, inclusive, and still further provided that when a 2-naphthyl is present, the pyridyl ring is other than the four position.

2. A compound of the formula

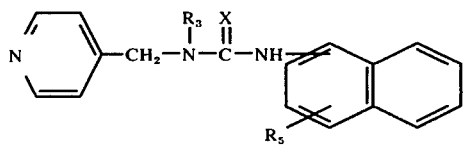

and pharmaceutically acceptable acid addition salts thereof wherein $R_3$ is hydrogen or alkyl of one to four carbon atoms, inclusive, $R_5$ is halogen, alkyl of one to four carbon atoms, inclusive, alkoxy of one to four carbon atoms, inclusive, or alkylthio of one to four carbon atoms, inclusive; and X is oxygen or sulfur.

3. A compound of the formula

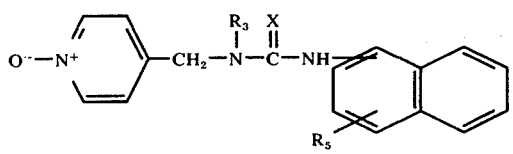

and pharmaceutically acceptable acid addition salts thereof wherein $R_3$ is hydrogen or alkyl of one to four carbon atoms, inclusive; $R_5$ is halogen, alkyl of one to four carbon atoms, inclusive, alkoxy of one to four carbon atoms, inclusive, or alkylthio of one to four carbon atoms, inclusive; and X is oxygen or sulfur.

4. A compound of the formula

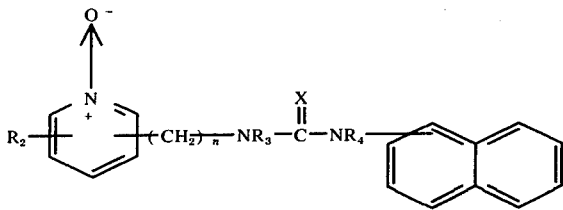

and pharmaceutically acceptable acid addition salts thereof wherein $R_2$ is hydrogen, alkyl of one to four carbon atoms, inclusive, or halogen; $R_3$ and $R_4$ are the same or different and are hydrogen or alkyl of one to four carbon atoms, inclusive; X is oxygen or sulfur; and n is one or two; provided that when $R_2$ and $R_4$ are hydrogen and X is sulfur, then $R_3$ is hydrogen and further provided that when $R_2$ is hydrogen or halogen, $R_4$ is hydrogen and X is oxygen, then $R_3$ is alkyl of one to four carbon atoms, inclusive; and still further provided that when a 2-naphthyl is present the pyridyl ring is other than the four position.

5. The compound of claim 1 which is 1-(1-naphthyl)-3-(4-pyridylmethyl)-2-thiourea.

6. The compound of claim 1 which is 1-(1-naphthyl)-3-(2-pyridylmethyl)-2-thiourea.

7. The compound of claim 1 which is 1-(1-naphthyl)-3-(3-pyridylmethyl)-2-thiourea.

8. The compound of claim 1 which is 1-(2-naphthyl)-3-(3-pyridylmethyl)-2-thiourea.

9. The compound of claim 1 which is 1-methyl-3-(1-naphthyl)-1-(2-pyridylethyl)urea.

10. The compound of claim 4 which is 1-(1-naphthyl)-3-(3-pyridylmethyl)urea-N-oxide.

11. The compound of claim 4 which is 1-(1-naphthyl)-3-(4-pyridylmethyl)urea-N-oxide.

12. 1-(2-naphthyl)-3-(2-pyridylmethyl)-2-thiourea.

13. 1-(2-naphthyl)-3-(4-pyridylmethyl)-2-thiourea.

14. A pharmaceutical dosage unit form, useful for increasing the production of endogenous prostaglandin $F_{2\alpha}$ by a mammal, which comprises an amount of a compound which is effective to increase the production of engodenous prostaglandin $F_{2\alpha}$ selected from the formula:

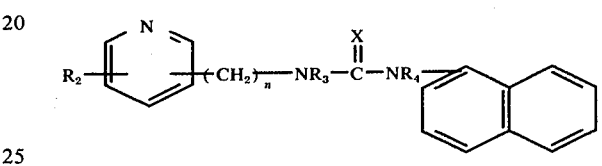

pyridyl N-oxides thereof and pharmaceutically acceptable acid addition salts thereof wherein $R_2$ is hydrogen, alkyl of one to four carbon atoms, inclusive, or halogen; $R_3$ and $R_4$ are the same or different and are hydrogen or alkyl of one to four carbon atoms, inclusive; X is oxygen or sulfur; and n is one or two; provided that when $R_2$ and $R_4$ are hydrogen and X is sulfur, then $R_3$ is hydrogen, and further provided that when $R_2$ is hydrogen or halogen, $R_4$ is hydrogen and X is oxygen, then $R_3$ is alkyl of one to four carbon atoms, inclusive, and still further provided that when a 2-naphthyl is present the pyridyl ring is other than the four position in association with a pharmaceutical carrier suitable for systemic administration.

15. A pharmaceutical dosage unit form, useful for increasing the production of endogenous prostaglandin $F_{2\alpha}$ by a mammal, which comprises an amount of a compound which is effective to increase the production of endogenous prostaglandin $F_{2\alpha}$ selected from the formula:

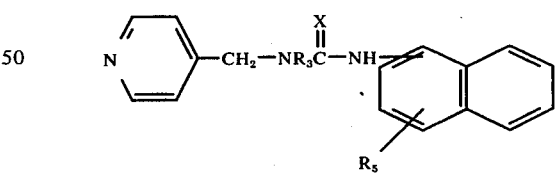

pyridyl N-oxides thereof and pharmaceutically acceptable acid addition salts thereof wherein $R_3$ is hydrogen or alkyl of one to four carbon atoms, inclusive; $R_5$ is halogen, alkyl of one to four carbon atoms, inclusive, alkoxy of one to four carbon atoms, inclusive, or alkylthio of one to four carbon atoms, inclusive; and X is oxygen or sulfur in association with a pharmaceutical carrier suitable for systemic administration.

* * * * *

UNITED STATES PATENT OFFICE
CERTIFICATE OF CORRECTION

Patent No. 4,008,326    Dated  15 February 1977

Inventor(s)   William A. Callahan, et al.

It is certified that error appears in the above-identified patent and that said Letters Patent are hereby corrected as shown below:

Column 3, line 52, "compounds (II" should read -- compounds (II) --;
Column 4, line 63, "Illustrative or aryloxy" should read -- Illustrative of aryloxy --;
Column 6, line 40 and line 43, "PGE$_2$ and PGF$_2$" should read -- PGE$_2$ and PGF$_2\alpha$ --;
Column 8, line 25, "PGF$_2$" should read -- PGF$_2\alpha$ --;
Column 10, lines 10-15,

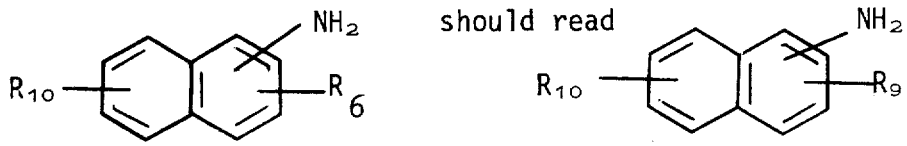

Column 14, line 22, "starchbentonite" should read -- starch, bentonite --;
Column 15, line 13, "1-naphthylisothiocyanate" should read -- 2-naphthylisothiocyanate --; line 61, "2-(aminomethyl-4-" should read -- 2-(aminomethyl)-4- --.

Signed and Sealed this

Twenty-first Day of July 1981

[SEAL]

Attest:

GERALD J. MOSSINGHOFF

Attesting Officer    Commissioner of Patents and Trademarks